United States Patent [19]

De Regis et al.

[11] Patent Number: 4,698,354
[45] Date of Patent: Oct. 6, 1987

[54] 4-METHOXY-ISOPHTHALIC ACID DERIVATIVE HAVING A PHARMACOLOGICAL ACTIVITY IN THROMBOEMBOLIC DISORDERS

[75] Inventors: Massimo De Regis, Sesto Fiorentino; Emanuela Mannucci, Florence, both of Italy

[73] Assignee: Societa Italo-Brittanica L. Manetti-H. Roberts & Co., Florence, Italy

[21] Appl. No.: 917,072

[22] Filed: Oct. 8, 1986

[30] Foreign Application Priority Data

Oct. 10, 1986 [IT] Italy ................... 9499 A/85

[51] Int. Cl.⁴ ................ A61K 31/44; C07D 211/04
[52] U.S. Cl. ..................... 514/357; 546/336
[58] Field of Search ............ 546/336; 514/357

[56] References Cited

U.S. PATENT DOCUMENTS 3,973,026  8/1976  Orzalesi ............... 514/357
4,294,833  10/1981 Innocenti ............. 514/357

FOREIGN PATENT DOCUMENTS 3113150  4/1981  Fed. Rep. of Germany ...... 546/336
7123901  3/1972  France ..................... 514/357
2080288  2/1986  United Kingdom ........... 514/357

Primary Examiner—Alan L. Rotman
Assistant Examiner—J. Richter
Attorney, Agent, or Firm—Cushman, Darby & Cushman

[57] ABSTRACT 3-carbamoyl-(3'-picolyl)-4-methoxy-1-benzamide of formula

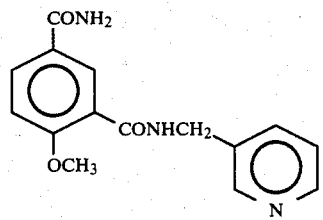

is a pharmaceutical agent for the prevention and treatment of thromboelmbolic disorders due to increased blood platelet aggregation.

3 Claims, 2 Drawing Figures

4-METHOXY-ISOPHTHALIC ACID DERIVATIVE HAVING A PHARMACOLOGICAL ACTIVITY IN THROMBOEMBOLIC DISORDERS

BACKGROUND OF THE INVENTION

1. Field of the Invention

The present invention relates to a novel organic substance included in the class comprising substituted or non-substituted isophthalic acid picolylamides, which is pharmacologically active and able to inhibit the blood platelet aggregation in vitro and in vivo and to control the thromboembolic disorders produced by a modified blood platelet reactivity.

The present invention also relates to a process for the synthesis of said substance.

The compound forming the object of the present invention is a 4-methoxy-isophthalic acid picolylamide whose chemical denomination is 3-carbamoyl(3'-picolyl)-4-methoxy-1-benzamide or, in an equivalent nomenclature, N-N'-(3'-picolyl)-4-methoxy-isophthalamide, the formula of which is $C_{15}H_{15}N_3O_3$ corresponding to a mole weight of 285,3.

The conventional structural formula thereof can be represented as follows:

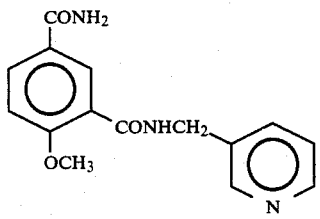

In the following description, the above defined compound will be briefly indicated as G 619.

2. Prior Art

It is well known, particularly from U.S. Pat. No. 3,973,026, Italian Pat. No. 1016005, U.S. Pat. No. 4,294,833 and German patent No. 3113150, that the organic compounds of the class comprising substituted or non-substituted isophthalic acid picolylamides show an anti-coagulant, fibrinolitic and blood platelet anti-aggregant activity. Among said compounds N-N'-bis-(3-picolyl)-4-methoxy-isophthalamide monohydrate under a crystal form has shown a particularly high activity (see German Pat. No. 3113150), which compound is briefly indicated with the denomination "picotamide monohydrate".

It has now been surprisingly found that the compound object of the present invention has a still higher and more rapid pharmacological activity of the same type, particularly as far as the inhibition of blood platelet aggregation is concerned. On the basis of the knowledge available at the state of the prior art for the compounds included in the above-mentioned class, and particularly for anhydrous picotamide and picotamide monohydrate, it was not to be expected as obvious that an elimination of the 3-picoline radical on the amide nitrogen atom in 1-position would produce a nett increase of the pharmacological activity and biodisposability, nor could it be expected that such activity increase would be free from negative side effects, as on the contrary it has resulted with the compound object of the present invention.

SUMMARY OF THE INVENTION

It is an object of the present invention to provide a novel 4-methoxy-isophthalic acid picolylamide which has a higher activity and pharmacological efficiency, in view of the positive effects found after absorbtion by the animal and human organism.

A further object of the present invention is a process for obtaining the above-mentioned novel substance.

Another object of the present invention is the therapeutical use of the above-mentioned novel substance under the various pharmacologically active forms thereof for preventing and treating thromboembolic diseases.

DETAILED DESCRIPTION OF THE INVENTION

The compound according to the present invention of the above illustrated formula, can be obtained by reacting a 4-methoxy-isophthalic monoloweralkyl ester with 3-picolylamine, so as to obtain the respective monopicolylamide. Then the mixed anhydride which is formed as an intermediate is reacted in an anhydrous solvent with ethylchloroformate, and in the presence of a proton acceptor and under an ammonia gas stream, it is possible to obtain the compound according to the invention.

The following schema illustrates the reactions:

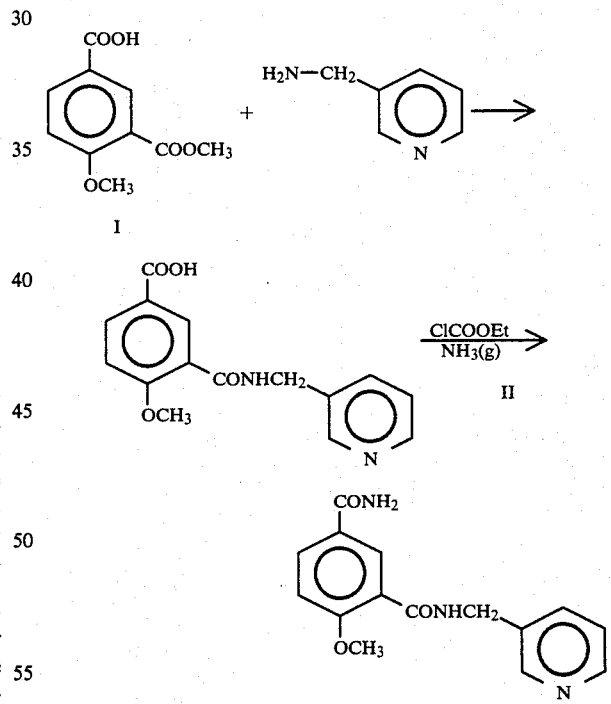

In the following preparation example which is merely illustrative and not limitative of the present invention, the process is described by which it is possible to obtain the product of the invention by synthesis. Possible modifications which are obvious to those skilled in the art, fall within the scope of the invention.

EXAMPLE OF PREPARATION (a) Step 1: synthesis of mono(3-picolylamide) (I).

A mixture of 4,7 ml 4-methoxy-isophthalic acid monomethylester and 47 ml of 3-picolylamine is maintained for 24 hours at a temperature of from 55° to 65° C., preferably 60° C. At the end of this time, it is cooled and the reaction container is placed in a freezing mixture such that the temperature is maintained about 0° C. during the following acidification, which is carried out by glacial acetic acid or with HCl 5N to the extent that a pH from 3,5 to 5,5 depending on the situation is reached, to obtain, in other words, the total precipitation of compound I. The precipitate is recovered by suction, thoroughly washed with distilled water and crystalized from organic solvent. It is used as such for the following step.

(b) Step 2: synthesis of 3-carbamoyl(3'-picolyl)-methoxy-1-benzamide (II).

A mixture of 2,6 ml of compound I, obtained as previously described and suspended into chloroform, with 5,6 mol triethylamine (as a proton acceptor), is slowly additioned with 5,6 ml ethylchloroformate under stirring at 0° C. After standing at 0° C. for half an hour, the reaction mixture is saturated by ammonia gas, then left at room temperature for three hours. At the end of this time, the white precipitate of the desired product (compound II) is recovered by suction filtering, washed with water and crystalized from a suitable solvent. The product thus obtained shows a melting point of 190°–191° C. at the Kofler bench.

The mole structure of G619 has been determined by X-ray analysis, by using an automatic diffractometer Enraf-Nonius CAD-4 having four circles with graphite monochromator. The data have been processed by a Gould SEL 32/27 computer and with the aid of a video terminal Tektronix 4125.

Figure 1:
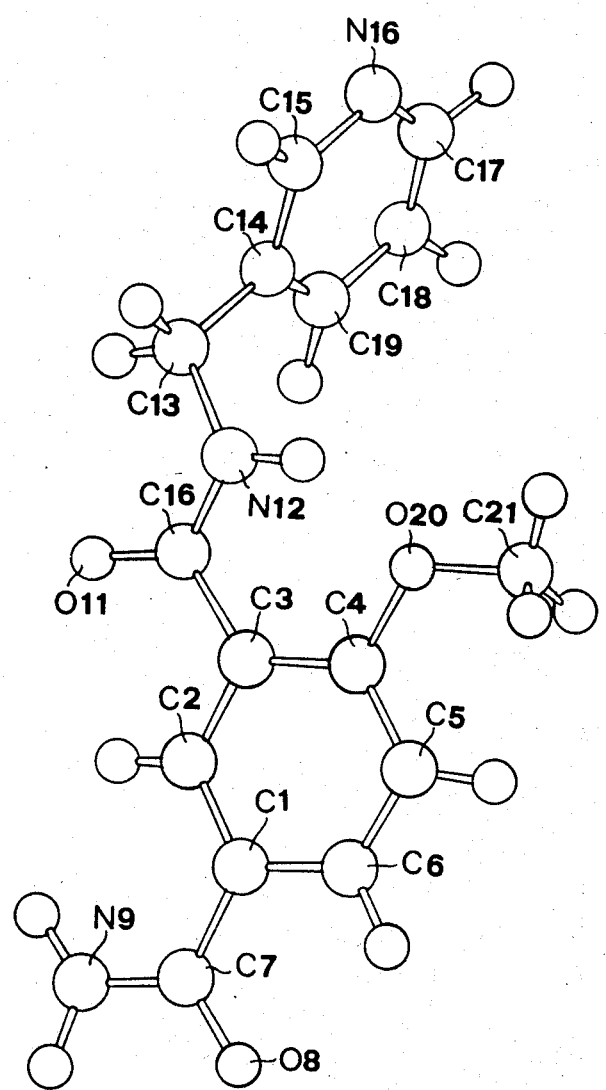

The structure of the molecule resulting from the analysis, is illustrated in FIG. 1.

Figure 2:
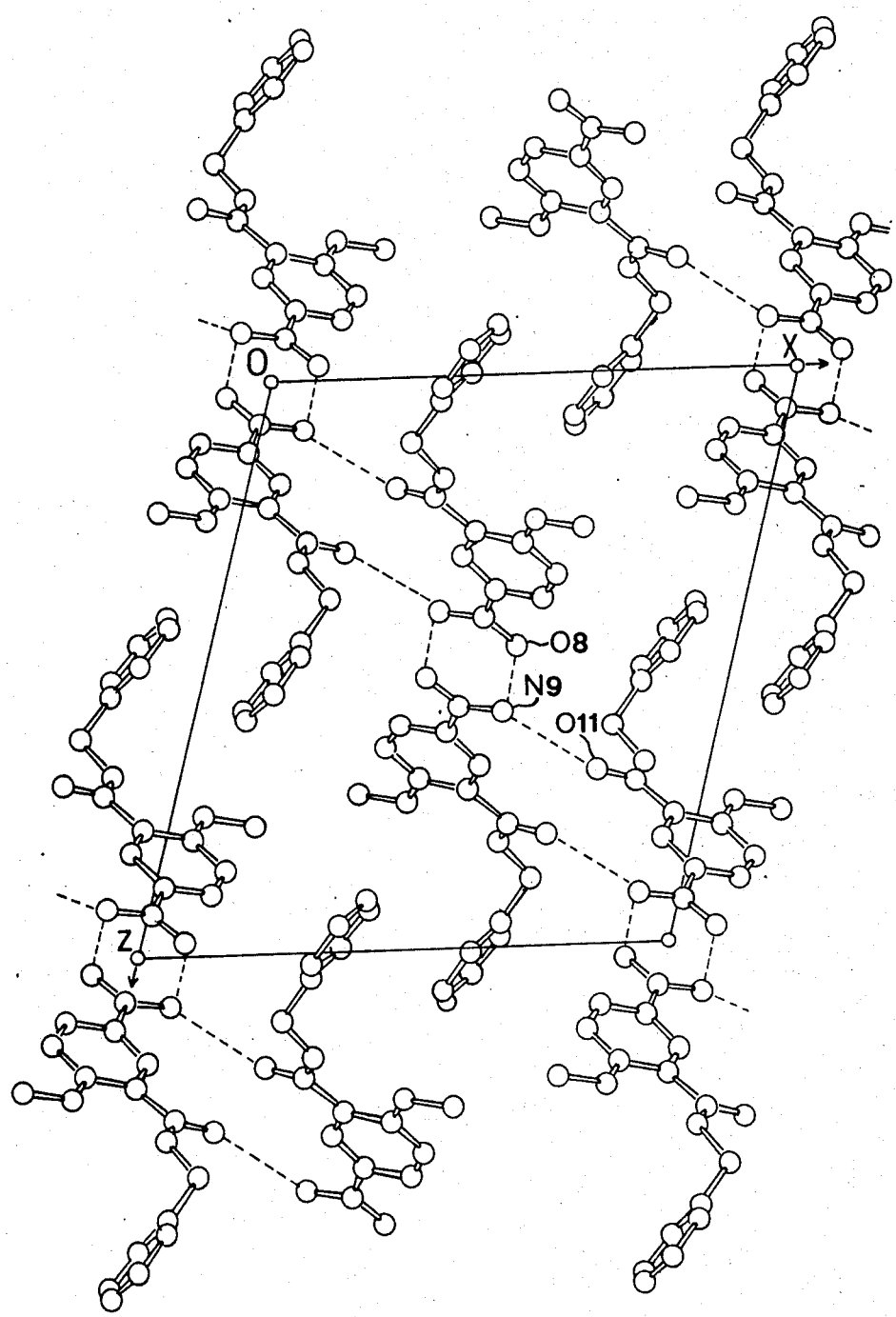

FIG. 2 represents the position of the molecules in the crystal in a projection perpendicular to the crystallographic axis y.

Each molecule is characterized by an intramolecular hydrogen bond between O20 and N12 (bond length 2.63 A) and two intermolecular hydrogen bonds both relating to the amide nitrogen N9 and oxygen O8 respectively of one molecule (bond length 2.94 A) and oxygen O11 of another molecule (bond length 2.95 A). The intermolecular hydrogen bonds are illustrated with dotted lines in FIG. 2.

The fractional atomic coordinates as well as the values of bond distances and angles relating to the molecule of G 619 are referred in the following tables.

TABLE I

FRACTIONAL ATOMIC COORDINATES FOR THE CARBON, OXYGEN, NITROGEN AND HYDROGEN ATOMS

| ATOM | X | Y | Z |
|---|---|---|---|
| C 1 | .0150 | −.5236 | .8759 |
| C 2 | −.0615 | −.4187 | .8163 |
| C 3 | −.0479 | −.2255 | .7762 |
| C 4 | .0479 | −.1403 | .7966 |
| C 5 | .1250 | −.2452 | .8540 |
| C 6 | .1081 | −.4339 | .8933 |
| C 7 | .0056 | −.7266 | .9247 |
| O 8 | .0799 | −.8046 | .9750 |
| N 9 | −.0825 | −.8167 | .9123 |
| C 10 | −.1376 | −.1282 | .7146 |
| O 11 | −.2159 | −.2265 | .6955 |
| N 12 | −.1287 | .0666 | .6817 |
| C 13 | −.2064 | .1787 | .6169 |
| C 14 | −.1679 | .2594 | .5413 |
| C 15 | −.1722 | .4734 | .5197 |
| N 16 | −.1373 | .5578 | .4544 |
| C 17 | −.0954 | .4216 | .4100 |

TABLE I-continued

FRACTIONAL ATOMIC COORDINATES FOR THE CARBON, OXYGEN, NITROGEN AND HYDROGEN ATOMS

| ATOM | X | Y | Z |
|---|---|---|---|
| C 18 | −.0886 | .2085 | .4250 |
| C 19 | −.1256 | .1245 | .4916 |
| O 20 | .0617 | .0503 | .7578 |
| C 21 | .1597 | .1325 | .7751 |
| H 2 | −.1265 | −.4817 | .8028 |
| H 5 | .1984 | −.1958 | .8708 |
| H 6 | .1649 | −.5188 | .9360 |
| H 91 | −.1429 | −.7513 | .8750 |
| H 92 | −.0819 | −.9553 | .9487 |
| H 12 | −.0654 | .1306 | .6998 |
| H 13 | −.2638 | .0706 | .5938 |
| H 13 | −.2412 | .3035 | .6469 |
| H 15 | −.1995 | .5800 | .5583 |
| H 17 | −.0627 | .4797 | .3634 |
| H 18 | −.0419 | .1037 | .3953 |
| H 19 | −.1225 | −.0590 | .5025 |
| H 21 | .2042 | .0168 | .7525 |
| H 21 | .1870 | .1621 | .8439 |
| H 21 | .1514 | .2662 | .7441 |

TABLE 2

| BOND DISTANCES (A) | |
|---|---|
| C1-C2 | 1.390 |
| C1-C6 | 1.387 |
| C1-C7 | 1.502 |
| C2-C3 | 1.395 |
| C3-C4 | 1.407 |
| C3-C10 | 1.502 |
| C4-C5 | 1.380 |
| C4-O20 | 1.372 |
| C5-C6 | 1.377 |
| C7-O8 | 1.233 |
| C7-N9 | 1.330 |
| C10-O11 | 1.229 |
| C10-N12 | 1.340 |
| N12-C13 | 1.460 |
| C13-C14 | 1.501 |
| C14-C15 | 1.378 |
| C14-C19 | 1.378 |
| C15-N16 | 1.345 |
| N16-C17 | 1.326 |
| C17-C18 | 1.353 |
| C18-C19 | 1.376 |
| O20-C21 | 1.431 |

TABLE 3

| BOND ANGLES | |
|---|---|
| C6-C1-C7 | 116.5 |
| C2-C1-C7 | 125.6 |
| C2-C1-C6 | 118.0 |
| C1-C2-C3 | 122.3 |
| C2-C3-C10 | 116.4 |
| C2-C3-C4 | 117.5 |
| C4-C3-C10 | 126.0 |
| C3-C4-O20 | 117.8 |
| C3-C4-C5 | 120.9 |
| C5-C4-O20 | 121.3 |
| C4-C5-C6 | 119.8 |
| C1-C6-C5 | 121.5 |
| C1-C7-N9 | 119.0 |
| C1-C7-O8 | 118.9 |
| O8-C7-N9 | 122.0 |
| C3-C10-N12 | 117.7 |
| C3-C10-O11 | 120.3 |
| O11-C10-N12 | 122.0 |
| C10-N12-C13 | 124.9 |
| N12-C13-C14 | 110.0 |
| C13-C14-C19 | 121.9 |
| C13-C14-C15 | 121.0 |
| C15-C14-C19 | 117.2 |
| C14-C15-N16 | 124.3 |
| C15-N16-C17 | 116.0 |

TABLE 3-continued

| BOND ANGLES | |
|---|---|
| N16-C17-C18 | 124.3 |
| C17-C18-C19 | 118.8 |
| C14-C19-C18 | 119.3 |
| C4-O20-C21 | 118.0 |

PHARMACOLOGICAL TESTS

The compound object of the present invention has been tested to ascertain the acute toxicity, bio-disponibility and interference with the blood platelet function in vitro and in vivo by carrying out tests in all cases in comparison with another molecule, picotamide monohydrate, which is included in the same class of products, and the pharmacological activity of which is already known (see German patent 3113150).

EXAMPLE 1

Blood platelet anti-aggregate activity in vitro.

Platelet aggregation was induced in rabbit "platelet rich plasma" (PRP) by employing as aggregant agents adenosine diphosphate (ADP) and arachidonic acid (AANa) after incubation at 37° C. for 10 minutes with the compounds under test. The activity is expressed as the concentration able to decrease by 50% ($IC_{50}$) the maximum amplitude (AM) of the aggregation curve so obtained, with respect to the aggregation curve as obtained with control plasmas incubated only with buffers.

The results of the tests effected with ADP and AANa are hereinafter referred:

Blood platelet aggregation from ADP

| | |
|---|---|
| G 619 | $IC_{50} = 1,25 \times 10^{-4}$ M |
| Picotamide monohydrate | $IC_{50} = 9,3 \times 10^{-4}$ M |

Blood platelet aggregation from AANa

| | |
|---|---|
| G619 | $IC_{50} = 2,69 \times 10^{-5}$ M |
| Picotamide monohydrate | $IC_{50} = 7,9 \times 10^{-5}$ M |

From the above illustrated results it can be observed that compound G 619 shows a platelet anti-aggregant activity which is from 3 to 7 times higher that that of picotamide monohydrate, depending on the aggregant agent used.

EXAMPLE 2

Blood platelet anti-aggregant activity in vivo.

New Zealand rabbits which had been held fasting for twelve hours with water ad libitum, were administered with G 619 and picotamide monohydrate at various dosages in a gum acacia suspension. To the control rabbits only gum acacia was administered. After 30 minutes from treatment the animals were anaesthetized with sodium pentothal (30 mg/Kg i.v.) and blood was taken from the carotid artery, rendered incoagulable with sodium citrate at 3,8% and centrifuged at 1400 rpm for 15 minutes in order to obtain the platelet rich plasma (PRP). On said PRP the platelet aggregation was induced by arachidonic acid and the corresponding aggregation curve was recorded using a Born aggregometer. The activity is indicated as the dose able to decrease by 50% ($ID_{50}$) the maximum amplitude (AM) of the aggregation curve of plasma of treated animals with respect to that of plasma from control animals, the following results being obtained:

| | |
|---|---|
| G 619 | $ID_{50} = 25$ mg/Kg |
| Picotamide monohydrate | $ID_{50} = 78$ mg/Kg |

From the above results it can be seen that the activity G 619 is about 3 times higher than that of picotamide monohydrate.

EXAMPLE 3

Per os absorbtion in rat

Per os absorbtion tests have been carried out in rat after a sole administration of 100 mg/Kg in gum acacia suspension. The determinations of the blood levels of the two substances at various times have been effected on plasma using a high pressure liquid phase chromotograph and indicated as $\gamma$/ml. The values referred hereinafter represent the average of 8 determinations:

| | $\frac{1}{2}$ h | 1 h | 2 h | 4 h |
|---|---|---|---|---|
| G 619 | 26,9 | 20,2 | 9,4 | 2,1 |
| Picotamide monohydrate | 3,4 | 1,2 | 0,5 | — |

It can be noted that compound G 619 shows an absorbtion from 8 ($\frac{1}{2}$ hour) to 19 times (2 hours) higher than that of picotamide monohydrate.

EXAMPLE 4

Acute toxicity ($DL_{50}$)

The compound of the present invention was subjected to acute toxicity tests on two animal species and two administration routes. The animals which are treated per os or endovenously in a sole administration, have been held under observation for seven days after treatment by recording the symptomatology and the number of deaths. The results, referred in the following table, are indicated as the dose which produces the death of 50% of the treated animals ($DL_{50}$) calculated by statistical method:

| | | G 619 | Picotamide monohydrate |
|---|---|---|---|
| Mouse | i.v. | 400 mg/Kg | 275 mg/Kg |
| | os | >3000 mg/Kg | 3000 mg/Kg |
| Rat | i.v. | 450 mg/Kg | 190 mg/Kg |
| | os | >3000 mg/Kg | 3000 mg/Kg |

It can be observed that toxicity, shown prevailingly with a depressive symptomatology, appears to be very low in proportion to the above mentioned pharmacological activity.

EXAMPLE 5

Blood platelet anti-aggregant activity in vitro on human blood and evaluation of the mechanism of action.

The blood platelet anti-aggregant activity of G619 was studied in comparison with picotamide on human platelet rich plasma (PRP), wherein the platelet aggregation was induced with ADP, collagen, AANa and U46619 after incubation at 37° C. for ten minutes with the compounds under test. The results, indicated as a concentration able to decrease by 50% ($IC_{50}$) the maximum amplitude of the aggregation curve obtained with control plasma incubated only with the buffer, are the following:

| Aggregant agent | G619 | Picotamide |
|---|---|---|
| ADP | $5.6 \times 10^{-5}$ | $8.2 \times 10^{-4}$ |
| Collagen | $1.1 \times 10^{-5}$ | $1.0 \times 10^{-4}$ |
| AANa | $4.2 \times 10^{-6}$ | $8.9 \times 10^{-5}$ |
| U46619 | $9.2 \times 10^{-6}$ | $2.5 \times 10^{-4}$ |

In order to investigate the mechanism of action of G619 the production of malondialdehyde (MDA) and thromboxane $B_2$ ($TxB_2$) after stimulation with collagen 1 µg/ml was measured on human PRP. The results, indicated as $IC_{50}$, are as follows:

| MDA | G619 | Picotamide |
|---|---|---|
| (mM:$10^9$ platelets) | $1 \times 10^{-4}$ | $5 \times 10^{-4}$ |
| T × $B_2$ (ug/ml) | $4.6 \times 10^{-6}$ | $1 \times 10^{-5}$ |

The production of 6-keto-PGFla was also measured after stimulation of human PRP with collagen 1 ug/ml. An increase by 100-150% in the production of 6-keto-PGFla was observed starting from concentrations of $10^{-6}$M, in correspondance with which picotamide showed itself to be hardly efficient.

The results show that G619 is a blood platelet antiaggregant agent with a power of action higher by a factor of 10 with respect to picotamide in platelet aggregations induced in human PRP.

EXAMPLE 6

Blood platelet anti-aggregant activity on human volounteers.

On healthy human volounteers of both sexes aging from 31 to 53 the blood anti-aggregant activity was evaluated by per os treatment at a 500 mg sole dose, taking the blood samples before treatment and after 1-2-4-6 hours. The platelet aggregation was induced in PRP using ADP as aggregant agent at a concentration of $2 \times 10^{-6}$M following the method illustrated in example 2. The platelet anti-aggregant activity reported in quantitative terms in the following table, was calculated as percent inhibition of the aggregation curve after treatment with respect to the

| control: | 1 h | 2 h | 4 h | 6 h |
|---|---|---|---|---|
| G 619 | 38,2 | 53,8 | 43,4 | 24,2 |
| Picotamide monohydrate | 18,2 | 25,6 | 41,1 | 21,5 |

The results as obtained and herein illustrated show in favour of G619 a higher and quicker platelet anti-aggregant activity, the maximum activity for G619 being namely of 53,8% and obtained after two hours after treatment, whereas for picotamide monohydrate a maximum of 41,1% was observed only after four hours.

CONCLUSIONS

The results as obtained and referred in the foregoing examples evidence substantial differences in positive activities in favour of compound G619 with respect to picotamide monohydrate. Moreover, this higher in vitro and in vivo pharmacological activity is associated to a lower toxicity and an improved biodisponibility as examples 3, 4 and 5 show. Furthermore, said substantial positive differences in favour of compound G619 were not to be expected on the basis of the simple elimination of 3-picoline radical on the nitrogen atom in 1 position.

Compound G619, in view of its high activity associated to low toxicity, excellent tollerability and biodisponibility, can be useful in human therapy for prevention and treatment of various thromboembolic disorders, particularly cerebro-vascular disorders, myocardial infarct, artery and phlebothrombosis, pulmonary embolism, general arteriosclerotic conditions, cardiosurgery and general surgery.

For said use various pharmaceutical forms can be employed, containing from 10 to 500 mg of active agent, examples of which can be mentioned merely as preferred embodiments:

(a) Orally: capsules, tablets, pills containing 10 to 500 mg, for a daily dosage of 50-2000 mg/day;

(b) Parenterally: sterilized endovenous and intramuscular injectable phials containing 10 to 50 mg for a daily dosage of 10 to 150 mg/day;

(c) Rectally: suppositories containing 10 to 500 mg for a daily dosage of 50 to 2000 mg/day.

The pharmaceutical formulation may obviously contain, besides the active agent, usual pharmaceutically acceptable vehicles and adjuvants, as is well known in the pharmaceutical field. It is also obvious that the administration forms of compound G619 and the respective dosage patterns can be varied according to the clinical circumstances and experience of physicians.

We claim:

1. 3-carbamoyl-(3'-picolyl)-4-methoxy-1-benzamide of formula:

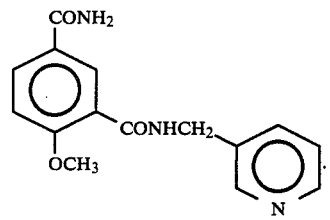

2. A method for preventing and treating thromboembolic disorders due to blood platelet aggregation in mammals, comprising administering an amount of 3-carbamoyl-(3'-picolyl)-4-methoxy-1-benzamide therapeutically effective to prevent and treat said disorders.

3. A pharmaceutical composition comprising an amount of 3-carbamoyl-(3'-picolyl)-4-methoxy-1-benzamide therapeutically effective for the prevention and treatment of thromboembolic disorders due to blood platelet aggregation, and a pharmaceutically compatible carrier.

* * * * *